(12) United States Patent
Daly et al.

(10) Patent No.: US 11,422,042 B2
(45) Date of Patent: Aug. 23, 2022

(54) FIBER OPTIC TEMPERATURE SENSORS IN A DISTRIBUTED SMOKE DETECTION SYSTEM

(71) Applicant: Kidde Technologies, Inc., Wilson, NC (US)

(72) Inventors: Amanda J. Daly, Cary, NC (US); Stefan Coreth, Roanoke Rapids, NC (US); Terry Simpson, Wake Forest, NC (US)

(73) Assignee: KIDDE TECHNOLOGIES, INC., Wilson, NC (US)

( * ) Notice: Subject to any disclaimer, the term of this patent is extended or adjusted under 35 U.S.C. 154(b) by 603 days.

(21) Appl. No.: 16/417,160

(22) Filed: May 20, 2019

(65) Prior Publication Data
US 2020/0370969 A1    Nov. 26, 2020

(51) Int. Cl.
*G01K 11/3206* (2021.01)
*B64F 5/60* (2017.01)
(Continued)

(52) U.S. Cl.
CPC ............ *G01K 11/3206* (2013.01); *B64F 5/60* (2017.01); *G01K 1/026* (2013.01); *G08B 17/107* (2013.01); *B64D 2045/009* (2013.01)

(58) Field of Classification Search
CPC .... G01K 11/32; G01K 11/3206; G01K 1/026; B64F 5/60; G08B 17/107; B64D 2045/009
See application file for complete search history.

(56) References Cited

U.S. PATENT DOCUMENTS

| 6,252,689 | B1 * | 6/2001 | Sharp | H04B 10/807 398/115 |
| 8,035,527 | B2 * | 10/2011 | Powell | G08B 17/113 340/606 |

(Continued)

FOREIGN PATENT DOCUMENTS

| EP | 3246683 A1 | 11/2017 |
| FR | 2868052 B1 | 9/2006 |

OTHER PUBLICATIONS

European Search Report for European Application No. 19212781.9, dated Jun. 30, 2020, 8 pages.

*Primary Examiner* — Nathaniel T Woodward
*Assistant Examiner* — Philip L Cotey
(74) *Attorney, Agent, or Firm* — Cantor Colburn LLP

(57) ABSTRACT

A smoke and temperature detection system includes a plurality of fiber optic cables terminating in a plurality of nodes positioned to monitor a fire or smoke condition at one or more protected spaces, and a temperature detection fiber optic cable having a plurality of fiber Bragg gratings arrayed along the temperature detection fiber optic cable. A control system is operably connected to the plurality of fiber optic cables and to the temperature detection fiber optic cable. The control system includes a first light sensitive device configured to receive a scattered light signal from the plurality of fiber optic cables, and a second light sensitive device configured to receive a reflected light signal from the fiber Bragg gratings. The control system is configured to detect a temperature at the fiber Bragg gratings based on one or more properties of the reflected light signal received at the second light sensitive device.

20 Claims, 3 Drawing Sheets

(51) Int. Cl.
*G01K 1/02* (2021.01)
*G08B 17/107* (2006.01)
*B64D 45/00* (2006.01)

(56) References Cited

U.S. PATENT DOCUMENTS

| | | | | |
|---|---|---|---|---|
| 9,799,186 | B2* | 10/2017 | Rennie | G08B 7/064 |
| 2006/0215959 | A1* | 9/2006 | McCarthy | G02B 6/02123 |
| | | | | 385/12 |
| 2009/0072981 | A1* | 3/2009 | Powell | G08B 17/06 |
| | | | | 385/12 |
| 2010/0290733 | A1* | 11/2010 | Xia | G01K 11/3206 |
| | | | | 156/60 |
| 2012/0186337 | A1* | 7/2012 | Guichard | G01P 5/10 |
| | | | | 73/204.23 |
| 2014/0266742 | A1* | 9/2014 | Rennie | G08B 7/064 |
| | | | | 340/584 |
| 2016/0236794 | A1* | 8/2016 | Tucker | B64D 45/00 |
| 2017/0336269 | A1* | 11/2017 | Wilson | G01K 11/3206 |
| 2018/0136053 | A1* | 5/2018 | Birnkrant | G01K 11/32 |
| 2018/0255385 | A1* | 9/2018 | Djordjevic | G01D 5/35383 |
| 2018/0340841 | A1* | 11/2018 | Coreth | G01K 11/3206 |

* cited by examiner

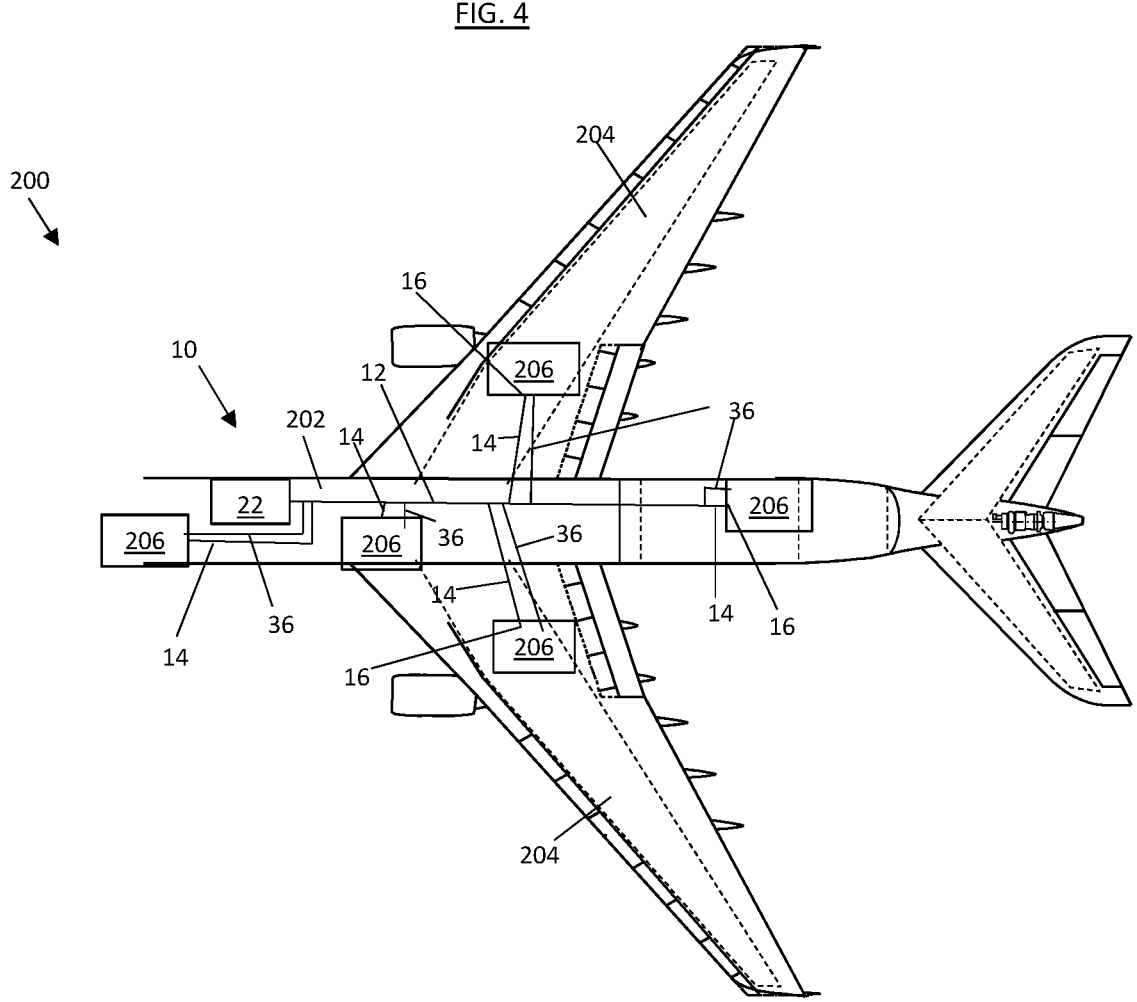

FIBER OPTIC TEMPERATURE SENSORS IN A DISTRIBUTED SMOKE DETECTION SYSTEM

BACKGROUND

The present disclosure relates to smoke detector systems for, for example, cargo bays of aircraft.

Currently, smoke detectors for cargo bays and other areas of aircraft sense temperature by utilizing electronic temperature sensors in order to maintain performance and control over temperature as well as indicate an alarm when the temperature reaches or exceeds a preselected threshold. These smoke detectors are self-contained line-replaceable units (LRUs), with all of the electronics for smoke detection and temperature monitoring contained within a package that is exposed to the elements of a typical cargo bay.

A smoke detection system is currently in development, including a centralized isolated controller which contains all of the electronic components of the smoke detection system, and a fiber network of smoke detection sensor nodes extending from the centralized controller that emit and receive light throughout a monitored area.

BRIEF SUMMARY

In one embodiment, a smoke and temperature detection system includes a plurality of fiber optic cables terminating in a plurality of nodes positioned to monitor a fire or smoke condition at one or more protected spaces, and a temperature detection fiber optic cable having a plurality of fiber Bragg gratings arrayed along the temperature detection fiber optic cable. A control system is operably connected to the plurality of fiber optic cables and to the temperature detection fiber optic cable. The control system includes a first light sensitive device configured to receive a scattered light signal from the plurality of fiber optic cables, and a second light sensitive device configured to receive a reflected light signal from the fiber Bragg gratings. The control system is configured to detect a temperature at the fiber Bragg gratings based on one or more properties of the reflected light signal received at the second light sensitive device.

Additionally or alternatively, in this or other embodiments the plurality of fiber Bragg gratings are located at the plurality of nodes.

Additionally or alternatively, in this or other embodiments the plurality of fiber Bragg gratings are arranged along the temperature detection fiber optic cable between the nodes.

Additionally or alternatively, in this or other embodiments the plurality of fiber Bragg gratings are substantially equally spaced along the temperature detection fiber optic cable.

Additionally or alternatively, in this or other embodiments the plurality of fiber Bragg sensors are spaced about one half meter apart.

Additionally or alternatively, in this or other embodiments a first light source is configured to transmit a first light signal along the plurality of fiber optic cables, and a second light source is configured to transmit a second light signal along the temperature detection fiber optic cable.

Additionally or alternatively, in this or other embodiments the second light sensitive device is a photodiode.

Additionally or alternatively, in this or other embodiments the plurality of compartments includes one or more of a cockpit, a cargo bay, or an electronics enclosure.

In yet another embodiment, a method of temperature detection for a monitored area includes extending a temperature detection fiber optic cable through the monitored area, arraying a plurality of fiber Bragg gratings along the temperature detection fiber optic cable, transmitting a light signal through the temperature detection fiber optic cable via a temperature detection light source, receiving a reflected light signal from the fiber Bragg gratings at a temperature detection light sensitive device, and detecting a temperature at the fiber Bragg gratings based on one or more properties of the reflected light signal.

Additionally or alternatively, in this or other embodiments the plurality of fiber Bragg gratings are located at one or more nodes of a fiber optic smoke detection system.

Additionally or alternatively, in this or other embodiments the plurality of fiber Bragg gratings are arranged along the temperature detection fiber optic cable between nodes of a fiber optic smoke detection system.

Additionally or alternatively, in this or other embodiments the plurality of fiber Bragg gratings are substantially equally spaced along the temperature detection fiber optic cable.

Additionally or alternatively, in this or other embodiments the temperature detection light source is a laser diode.

Additionally or alternatively, in this or other embodiments the temperature detection light sensitive device is a photodiode.

BRIEF DESCRIPTION OF THE DRAWINGS

The subject matter, which is regarded as the present disclosure, is particularly pointed out and distinctly claimed in the claims at the conclusion of the specification. The foregoing and other features, and advantages of the present disclosure are apparent from the following detailed description taken in conjunction with the accompanying drawings in which:

FIG. 4 is a schematic illustration of an aircraft including a detection system.

The detailed description explains embodiments of the present disclosure, together with advantages and features, by way of example with reference to the drawings.

DETAILED DESCRIPTION

Referring now to the FIGS., a system 10 for detecting one or more conditions or events within a designated area is illustrated. The detection system 20 may be able to detect one or more hazardous conditions, including but not limited to the presence of smoke, fire, flame, or any of a plurality of pollutants, combustion products, or chemicals. Alternatively, or in addition, the detection system 10 may be configured to perform monitoring operations of people, lighting conditions, or objects. In an embodiment, the system 10 may operate in a manner similar to a motion sensor, such as to detect the presence of a person, occupants, or unauthorized access to the designated area for example. The conditions and events described herein are intended as an example only, and other suitable conditions or events are within the scope of the disclosure.

The detection system 10 uses light to evaluate a volume for the presence of a condition. In this specification, the term "light" means coherent or incoherent radiation at any frequency or a combination of frequencies in the electromagnetic spectrum. In an example, the photoelectric system uses light scattering to determine the presence of particles in the ambient atmosphere to indicate the existence of a predetermined condition or event. In this specification, the term "scattered light" may include any change to the amplitude/intensity or direction of the incident light, including reflection, refraction, diffraction, absorption, and scattering in any/all directions. In this example, light is emitted in the designated area; when the light encounters an object (a person, smoke particle, or gas molecule for example), the light can be scattered and/or absorbed due to a difference in the refractive index of the object compared to the surrounding medium (air). Depending on the object, the light can be scattered in all directions. Observing any changes in the incident light, by detecting light scattered by an object for example, can provide information about the designated area including determining the presence of a predetermined condition or event.

Figure 1:
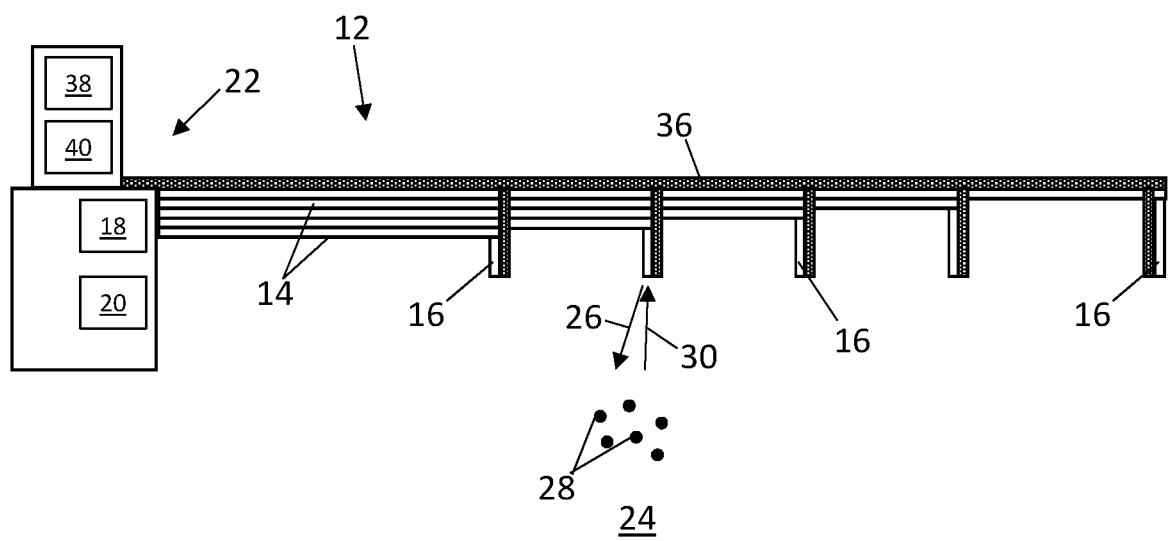
FIG. 1 is schematic diagram of an embodiment of a detection system according to an embodiment.

In its most basic form, as shown in FIG. 1, the detection system 10 includes a cable bundle 12 having a plurality of fiber optic cables 14 utilized for smoke detection. Each of the fiber optic cables 14 terminate at a node 16. The term fiber optic cable 14 includes any form of optical fiber. As examples, an optical fiber is a length of cable that includes of one or more optical fiber cores of single-mode, multimode, polarization maintaining, photonic crystal fiber or hollow core. A node 16 is located at the termination point of a fiber optic cable 14 and is inherently included in the definition of a fiber optic cable 14. The node 16 is positioned in communication with the ambient atmosphere. A light source 18, such as a laser diode for example, and a light sensitive device 20, such as a photodiode for example, are coupled to the fiber optic cable 14. While in some embodiments, each node 16 is associated with and operably connected to the same light sensitive device 20, in other embodiments each node 16 may be associated with and operably connected to a separate and distinct light sensitive device 20. A control system 22 of the detection system 10, is utilized to manage the detection system 10 operation and may include control of components, data acquisition, data processing and data analysis.

As shown in FIG. 1, the light 26 from the light source 18 is transmitted through the nodes 16 to the respective surrounding areas, illustrated schematically at 24. The light 26 interacts with one or more particles indicative of a condition, illustrated schematically at 28, and is reflected or transmitted back to the nodes 16, illustrated schematically at 30. A comparison of the light provided to the node 16 and/or changes to the light reflected back to the light sensitive device 20 from the nodes 16 will indicate whether or not changes in the atmosphere are present in the ambient atmosphere adjacent the node 16 that are causing the scattering of the light. The scattered light as described herein is intended to additionally include reflected, transmitted, and absorbed light. Although the detection system 10 is described as using light scattering to determine a condition or event, embodiments where light obscuration, absorption, and fluorescence is used in addition to or in place of light scattering are also within the scope of the disclosure.

In embodiments where a single light sensitive device 20 is configured to receive scattered light from a plurality of nodes 16, the control system 22 is able to localize the scattered light, i.e. identify the scattered light received from each of the plurality of nodes 16. In an embodiment, the control system 22 uses the position of each node 16, specifically the length of the fiber optic cables 14 associated with each node 16 and the corresponding time of flight (i.e. the time elapsed between when the light was emitted by the light source 18 and when the light was received by the light sensitive device 20), to associate different parts of the light signal with each of the respective nodes 16 that are connected to the light sensitive device 20. Alternatively, or in addition, the time of flight may include the time elapsed between when the light is emitted from the node and when the scattered light is received back at the node 16. In such embodiments, the time of flight provides information regarding the distance of the object relative to the node.

Figure 2:
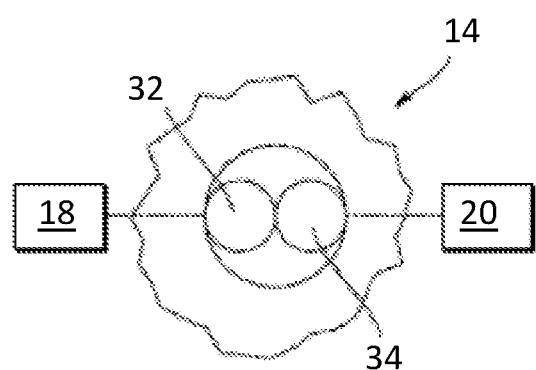
FIG. 2 is a cross-sectional view of an embodiment of a fiber optic cable.

In an embodiment, illustrated in the cross-section of the fiber optic cable 14 shown in FIG. 2, two substantially identical and parallel light transmission fiber cores 32, 34 are included in the fiber optic cable 14 and terminate at the node 16. However, it should be understood that embodiments where the fiber optic cable 14 includes only a single fiber core, or more than two cores are also contemplated herein. The light source 18 may be coupled to the first fiber core 32 and the light sensitive device 20 may be coupled to the second fiber core 34, for example near a first end of the fiber optic cable 14. The light source 18 is selectively operable to emit light, which travels down the first fiber core 32 of the fiber optic cable 14 to the node 16. At the node 16, the emitted light is expelled into the adjacent atmosphere. The light is scattered and transmitted back into the node 16 and down the fiber cable 14 to the light sensitive device 20 via the second fiber core 34.

Referring again to FIG. 1, the detection system 10 includes one or more temperature detection fiber optic cables 36 integrated into the cable bundle 12. The temperature detection fiber optic cables 36 extend to each node 16 and are connected to a dedicated temperature detection light source 38 and a dedicated temperature detection light sensitive device 40.

Figure 3:
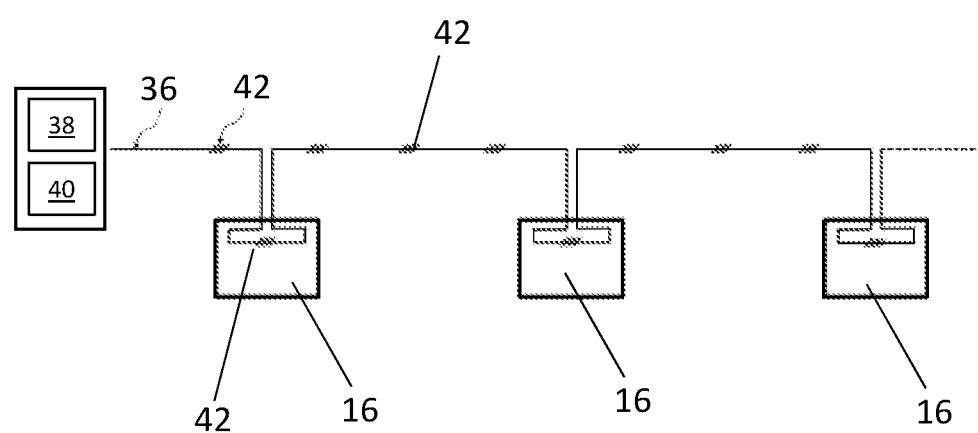
FIG. 3 is a schematic of a temperature detection fiber optic cable of an embodiment of a detection system.

For further description of the temperature detection fiber optic cable 36, we refer to FIG. 3, illustrating the detection system 10 with the fiber optic cables removed 14 for clarity. The temperature detection fiber cable 36 includes a plurality of fiber Bragg gratings 42 that are positioned along a length of the temperature detection fiber optic cable 36. In some embodiments, fiber Bragg gratings 42 are positioned at each node 16 location, and may additionally be arrayed along the temperature detection fiber optic cable 36 between the nodes 16, at a selected interval such as, for example, every half meter along the temperature detection fiber optic cable 36. The fiber Bragg gratings 42 may be equally-spaced as shown in FIG. 3, or alternatively a spacing between fiber Bragg gratings 42 may be varied to provide temperature detection at selected locations along the temperature detection fiber optic cable 36. Light is transmitted along the temperature detection fiber optic cable 36 from the temperature detection light source 38, and is reflected back along the temperature detection fiber optic cable 36 by the fiber Bragg gratings 42 to the temperature detection light sensitive device 40. Properties of the reflected light change with temperature, so changes in the reflected light captured at the temperature detection light sensitive device 40 are indicative of changes in temperature. More specifically, the control system 22 is configured to determine a temperature at each fiber Bragg grating 42 location based on the properties of the light received at the temperature detection light sensitive device 40. The temperature detection fiber optic cable 36 has strain relief from the node 16 itself, such that an accurate temperature measurement is obtained.

The separate temperature detection fiber optic cable 36 allows for independent temperature measurements, without possibility of interference with the smoke detection operation of the fiber optic cables 14. Further, the temperature detection fiber optic cable 36 reduces the impact of electromagnetic interference (EMI) and reduces cost and weight of the temperature detection system.

Referring now to FIG. 4, shown is a schematic view of an aircraft 200. The aircraft 200 includes a fuselage 202 with wings 204 extending therefrom. A plurality of monitored locations 206, such as a cockpit, cargo bay, electronics enclosures or the like, are distributed throughout the aircraft 200. It is desired to monitor the locations 206 for the presence of smoke, as well as monitor the temperatures of such locations 206 via the system 10. One or more nodes 16 are located in each monitored location 206, and the fiber optic cables 14 and temperature detection fiber optic cables 36 are routed therethrough. One skilled in the art will readily appreciate that the listed components are merely exemplary, and that further the components may be utilized in other vehicles or structures other than aircraft 200.

Embodiments of detection system 10 are installed in the aircraft 200 to detect fire, smoke and/or heat at the electronic devices 206. As shown in FIG. 4, the fiber optic cables 14 and the temperature detection fiber optic cables 36 are connected to control system 22, for managing operation of the system 10 to command the transmission of light signals and also analyze the returning light signals. When smoke is detected through operation of the fiber optic cables 14, or when a temperature detected along the temperature detection fiber optic cables 36 exceeds a selected threshold, the control system 22 may take one or more actions such as signaling an alarm to the cockpit crew of the aircraft 200 and/or initiating fire suppression or cooling operations.

While the disclosure has been described in detail in connection with only a limited number of embodiments, it should be readily understood that the disclosure is not limited to such disclosed embodiments. Rather, the invention can be modified to incorporate any number of variations, alterations, substitutions or equivalent arrangements not heretofore described, but which are commensurate with the spirit and scope of the disclosure. Additionally, while various embodiments of the disclosure have been described, it is to be understood that aspects of the disclosure may include only some of the described embodiments. Accordingly, the disclosure is not to be seen as limited by the foregoing description, but is only limited by the scope of the appended claims.

What is claimed is:

1. A smoke and temperature detection system, comprising:
    a plurality of fiber optic cables extending from a first end and terminating in a plurality of nodes disposed to monitor a smoke condition at one or more protected spaces;
    a temperature detection fiber optic cable separate and distinct from the plurality of fiber optic cables having a plurality of fiber Bragg gratings arrayed along the temperature detection fiber optic cable between the first end and the plurality of nodes;
    a control system operably connected to the plurality of fiber optic cables and to the temperature detection fiber optic cable, including:
        a first light sensitive device configured to receive a scattered light signal from the plurality of fiber optic cables; and
        a second light sensitive device configured to receive a reflected light signal from the fiber Bragg gratings;
        wherein the control system is configured to detect a temperature at the fiber Bragg gratings based on one or more properties of the reflected light signal received at the second light sensitive device.

2. The smoke and temperature detection system according to claim 1, wherein the plurality of fiber Bragg gratings are disposed at the plurality of nodes.

3. The smoke and temperature detection system according to claim 1, wherein the plurality of fiber Bragg gratings are arranged along the temperature detection fiber optic cable between the nodes.

4. The smoke and temperature detection system according to claim 3, wherein the plurality of fiber Bragg gratings are substantially equally spaced along the temperature detection fiber optic cable.

5. The smoke and temperature detection system according to claim 1, further comprising:
    a first light source configured to transmit a first light signal along the plurality of fiber optic cables; and
    a second light source configured to transmit a second light signal along the temperature detection fiber optic cable.

6. The smoke and temperature detection system according to claim 1, wherein the second light sensitive device is a photodiode.

7. An aircraft, comprising:
    a fuselage including one or more compartments; and
    a smoke and temperature detection system, including:
        a plurality of fiber optic cables extending from a first end and terminating in a plurality of nodes disposed to monitor a smoke condition at the one or more compartments;
        a temperature detection fiber optic cable separate and distinct from the plurality of fiber optic cables having a plurality of fiber Bragg gratings arrayed along the temperature detection fiber optic cable between the first end and the plurality of nodes;

a control system operably connected to the plurality of fiber optic cables and to the temperature detection fiber optic cable, including:

a first light sensitive device configured to receive a scattered light signal from the plurality of fiber optic cables; and a second light sensitive device configured to receive a reflected light signal from the fiber Bragg gratings;

wherein the control system is configured to detect a temperature at the fiber Bragg gratings based on one or more properties of the reflected light signal received at the second light sensitive device.

8. The aircraft according to claim 7, wherein the plurality of fiber Bragg gratings are disposed at the plurality of nodes.

9. The aircraft according to claim 7, wherein the plurality of fiber Bragg gratings are arranged along the temperature detection fiber optic cable between the nodes.

10. The aircraft according to claim 9, wherein the plurality of fiber Bragg gratings are substantially equally spaced along the temperature detection fiber optic cable.

11. The aircraft according to claim 10, wherein the plurality of fiber Bragg sensors are spaced about one half meter apart.

12. The aircraft according to claim 7, further comprising:

a first light source configured to transmit a first light signal along the plurality of fiber optic cables; and a second light source configured to transmit a second light signal along the temperature detection fiber optic cable.

13. The aircraft according to claim 7, wherein the second light sensitive device is a photodiode.

14. The aircraft according to claim 7, wherein the plurality of compartments includes one or more of a cockpit, a cargo bay, or an electronics enclosure.

15. A method of smoke and temperature detection for a monitored area, comprising:

extending a plurality of fiber optic cables extending from a first end and terminating in a plurality of nodes;

receiving a scattered light signal from the plurality of fiber optic cables at a first light sensitive device;

monitoring a smoke condition at the monitored area via the scattered light signal;

extending a temperature detection fiber optic cable separate and distinct from the plurality of fiber optic cables through the monitored area;

arraying a plurality of fiber Bragg gratings along the temperature detection fiber optic cable between a first end and a plurality of nodes;

transmitting a light signal through the temperature detection fiber optic cable via a temperature detection light source;

receiving a reflected light signal from the fiber Bragg gratings at a second light sensitive device; and detecting a temperature at the fiber Bragg gratings based on one or more properties of the reflected light signal.

16. The method according to claim 15, wherein the plurality of fiber Bragg gratings are disposed at one or more nodes of a fiber optic smoke detection system.

17. The method according to claim 15, wherein the plurality of fiber Bragg gratings are arranged along the temperature detection fiber optic cable between nodes of a fiber optic smoke detection system.

18. The method according to claim 17, wherein the plurality of fiber Bragg gratings are substantially equally spaced along the temperature detection fiber optic cable.

19. The method according to claim 15, wherein the temperature detection light source is a laser diode.

20. The method according to claim 15, wherein the temperature detection light sensitive device is a photodiode.

* * * * *